United States Patent
Tuppen et al.

(10) Patent No.: US 10,106,876 B2
(45) Date of Patent: Oct. 23, 2018

(54) METHOD OF SURFACE-TREATING A CAST INTERMETALLIC COMPONENT

(71) Applicant: ROLLS-ROYCE plc, London (GB)

(72) Inventors: Stephen John Tuppen, Swadlincote (GB); Daniel Clark, Belper (GB)

(73) Assignee: ROLLS-ROYCE plc, London (GB)

( * ) Notice: Subject to any disclaimer, the term of this patent is extended or adjusted under 35 U.S.C. 154(b) by 352 days.

(21) Appl. No.: 14/966,237

(22) Filed: Dec. 11, 2015

(65) Prior Publication Data
US 2016/0201181 A1    Jul. 14, 2016

(30) Foreign Application Priority Data
Jan. 9, 2015    (GB) .................................. 1500304.9

(51) Int. Cl.
*B23K 26/08*    (2014.01)
*C22F 1/18*    (2006.01)
(Continued)

(52) U.S. Cl.
CPC .......... *C22F 1/183* (2013.01); *B23K 26/0006* (2013.01); *B23K 26/0081* (2013.01); *B23K 26/08* (2013.01); *B23K 26/123* (2013.01); *B23K 26/1224* (2015.10); *B23K 26/354* (2015.10); *C21D 1/34* (2013.01); *C21D 1/74* (2013.01); *C21D 9/0068* (2013.01); *C22C 14/00* (2013.01); *C22F 1/02* (2013.01); *F01D 5/286* (2013.01); *G01N 21/95* (2013.01); *G01N 23/04* (2013.01);
(Continued)

(58) Field of Classification Search
CPC .................................. C22C 14/00; C22F 1/183
See application file for complete search history.

(56) References Cited

U.S. PATENT DOCUMENTS

| 4,195,913 A | 4/1980 | Dourte et al. |
| 4,348,263 A * | 9/1982 | Draper ..................... C25D 5/34 |
| | | 148/DIG. 93 |

(Continued)

FOREIGN PATENT DOCUMENTS

| EP | 1340567 A1 | 9/2003 |
| EP | 1952932 A2 | 8/2008 |
| WO | 2012/103933 A1 | 8/2012 |
| WO | 2014/149122 A2 | 9/2014 |

OTHER PUBLICATIONS

Jun. 6, 2016 Search Report issued in European Patent Application No. 15 19 9522.
(Continued)

*Primary Examiner* — Scott R Kastler
(74) *Attorney, Agent, or Firm* — Oliff PLC

(57) ABSTRACT

There is proposed a method of surface-treating a cast intermetallic component, which is intended primarily to reduce or remove surface porosity from the component. The method includes the steps of: providing a cast intermetallic component; placing the component in an inert atmosphere; focussing a laser beam on a surface of the component; traversing the laser beam over at least a region of said surface while the component is in said inert atmosphere; and controlling the laser beam during said traversing step so as to locally melt the intermetallic material of the component to a depth of no more than 300 μm, as measured from said surface of the component.

21 Claims, 2 Drawing Sheets

(51) Int. Cl.
- *C21D 1/34* (2006.01)
- *C21D 1/74* (2006.01)
- *C21D 9/00* (2006.01)
- *C22C 14/00* (2006.01)
- *C22F 1/02* (2006.01)
- *G01N 21/95* (2006.01)
- *G01N 23/04* (2018.01)
- *B23K 26/00* (2014.01)
- *B23K 26/12* (2014.01)
- *F01D 5/28* (2006.01)
- *B23K 26/354* (2014.01)
- *B23K 101/00* (2006.01)
- *B23K 103/10* (2006.01)
- *B23K 103/14* (2006.01)

(52) U.S. Cl.
CPC .... *B23K 2201/001* (2013.01); *B23K 2203/10* (2013.01); *B23K 2203/14* (2013.01)

(56) References Cited

U.S. PATENT DOCUMENTS

| | | |
|---|---|---|
| 5,167,734 A | 12/1992 | Mueller et al. |
| 5,609,470 A | 3/1997 | Dodd |
| 6,702,891 B2 | 3/2004 | Chiba |
| 7,630,423 B2 | 12/2009 | Ushinsky et al. |
| 7,675,952 B2 | 3/2010 | Ushinsky et al. |
| 7,722,793 B2 | 5/2010 | Gueguen et al. |
| 2002/0166844 A1 | 11/2002 | Kelly |
| 2014/0202997 A1 | 7/2014 | Vadali et al. |
| 2016/0201181 A1* | 7/2016 | Tuppen ............... C22F 1/183 148/510 |

OTHER PUBLICATIONS

Oct. 13, 2015 Search Report issued in British Patent Application No. 1500304.9.

* cited by examiner

METHOD OF SURFACE-TREATING A CAST INTERMETALLIC COMPONENT

The present invention relates to a method of surface-treating a cast intermetallic component. Embodiments of the invention are particularly, although not exclusively, suitable for treating cast intermetallic components such as turbine blades in gas turbine engines.

Intermetallic materials such as intermetallic titanium, and in particular gamma titanium aluminide (TiAl), have been proposed for or are currently used in the manufacture of high performance components in gas turbine engines used for aircraft propulsion. Examples of such components for which intermetallic materials are considered suitable include turbine blades and potentially also nozzle guide vanes. The properties of intermetallic materials such as gamma TiAl which make them particularly suitable for such components include its high specific strength, low density, and high melting point relative to conventional wrought titanium alloys which have been used previously. However, intermetallic materials tend to have limited ductility and fracture toughness, which presents a number of challenges when considering appropriate processing techniques for component manufacture and maintenance.

It has been proposed to manufacture gamma TiAl turbine blades via a conventional casting process, following by hot isostatic pressing (HIP). A typical issue with the casting process is the creation of inherent pores in the casting. When porosity is located in the region of a component's surface, typical surface finishing operations such as machining and vibro-polishing can result in pores becoming exposed to the surface. In extreme cases this can lead to highly undesirable surface-connected porosity, which in turn results in the component having reduced fatigue strength.

Conventionally, a limited degree of surface-connected or near-surface porosity in a cast intermetallic turbine blade is deemed acceptable if it is below a predetermined threshold. However, if such porosity arising from the casting process is above the threshold limit, then the component must be scrapped.

Hot isostatic pressing has been proposed as a post-casting technique to try to reduce the size of casting pores. Whilst this is effective in reducing the size of pores in the bulk material of a cast component, this technique has been found to give poor results in the specific case of surface-connected porosity because it results in significant undulations in the surface of the component where the pores are located, which is clearly undesirable for a high-performance aerodynamic component such as a turbine blade.

It is an object of the present invention to provide an improved method of surface-treating a cast intermetallic component.

According to the present invention, there is provided a method of surface-treating a cast intermetallic component, the method comprising the steps of: providing a cast intermetallic component; placing the component in an inert atmosphere; focussing a laser beam on a surface of the component; traversing the laser beam over at least a region of said surface whilst the component is in said inert atmosphere; and controlling the laser beam during said traversing step so as to locally melt the intermetallic material of the component to a depth of no more than 300 μm, as measured from said surface of the component.

Preferably, the laser beam is controlled so as to locally melt the intermetallic material of the component to a depth of no more than 150 μm as measured from said surface of the component.

The method may optionally further include a step of analysing the component, prior to said steps of focussing and traversing the laser beam, in order to identify target surface-connected and/or near-surface pores in the component and determine the maximum depth of said target pores from the surface of the component; wherein said step of controlling the laser beam involves operating the laser beam so as to locally melt the intermetallic material of the component to said maximum depth.

Said step of analysing the component may involve capturing an image of the surface region of the component.

Said image may optionally be a stereo-optical image.

Said image may alternatively be an X-ray image.

Advantageously, said step of controlling the laser beam involves controlling the laser beam in dependence on features of said image.

Conveniently, said step of analysing the component is performed manually.

Alternatively, said step of analysing the component is performed automatically using a computer.

In a preferred embodiment, said focussing step involves focussing the laser beam such that it energizes a target area on the surface of the component, and wherein said step of traversing involves moving the laser beam incrementally relative to the component so as to energize successive said target areas on the surface of the component; each target area being energized for a discrete dwell period and overlapping at least the immediately preceding target area.

Said step of traversing may involve movement of the laser beam.

Alternatively, or additionally, said step of traversing may involve movement of the component.

Conveniently, a heat load is applied to said component during said focussing, traversing and controlling steps, said heat load being applied to the opposite side of the component to that on which said surface is provided.

Optionally, said component is pre-tensioned during said focussing, traversing and controlling steps.

Said step of controlling the laser beam may involve controlling at least one of: the power; the focus; the beam-shape; and the pulse period of the laser beam.

The method may be performed on a component which is formed of intermetallic titanium.

The method may be performed on a component which is formed of gamma titanium aluminide.

The component is optionally provided in the form of a turbine blade for a gas turbine engine.

Conveniently, said step of placing the component in an inert atmosphere involves placing the component in a vacuum chamber. However, alternatively, the component could be positioned inside an gas shield formed from argon gas or another inert gas.

The method may involve the use of a plurality of said laser beams.

The method may be performed simultaneously on a plurality of said components.

So that the invention may be more readily understood, and so that further features thereof may be appreciated, embodiments of the invention will now be described by way of example with reference to the accompanying drawings in which.

Figure 1:
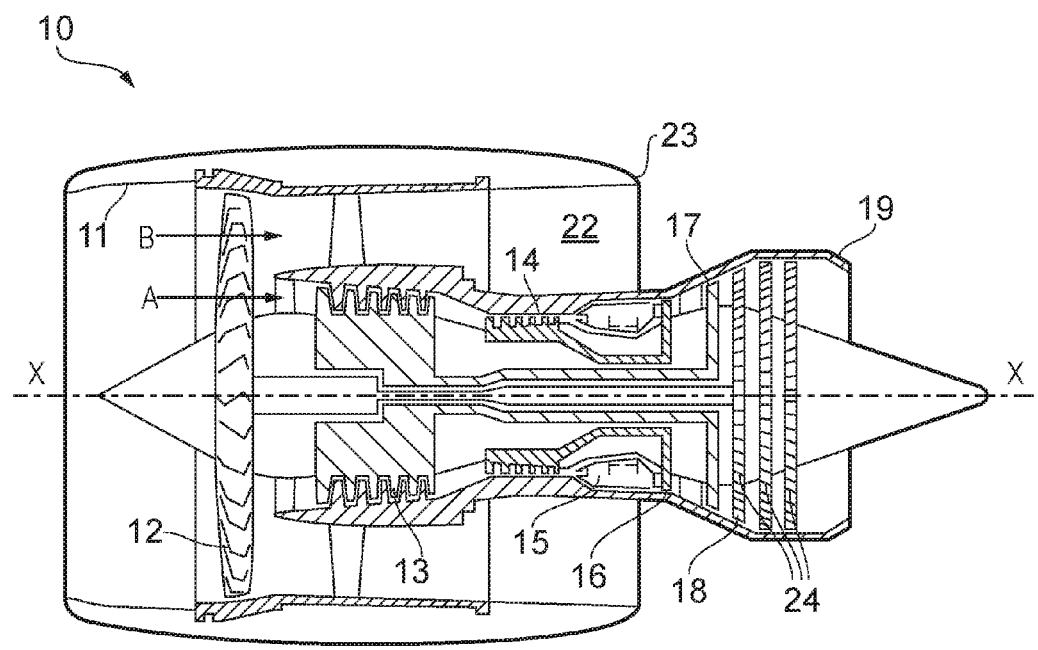
FIG. 1 is a schematic longitudinal cross-sectional view through a ducted fan gas turbine engine.

Turning now to consider the drawings in more detail, FIG. 1 illustrates a ducted fan gas turbine engine 10 having a principal and rotational axis X-X. The engine comprises, in axial flow series, an air intake 11, a propulsive fan 12, an intermediate pressure compressor 13, a high-pressure compressor 14, combustion equipment 15, a high-pressure turbine 16, an intermediate pressure turbine 17, a low-pressure turbine 18 and a core engine exhaust nozzle 19. A nacelle 21 generally surrounds the engine 10 and defines the intake 11, a bypass duct 22 and a bypass exhaust nozzle 23.

During operation, air entering the intake 11 is accelerated by the fan 12 to produce two air flows: a first air flow A into the intermediate pressure compressor 13 and a second air flow B which passes through the bypass duct 22 to provide propulsive thrust. The intermediate pressure compressor 13 compresses the air flow A directed into it before delivering that air to the high pressure compressor 14 where further compression takes place.

The compressed air exhausted from the high-pressure compressor 14 is directed into the combustion equipment 15 where it is mixed with fuel and the mixture combusted. The resultant hot combustion products then expand through, and thereby drive the high, intermediate and low-pressure turbines 16, 17, 18 before being exhausted through the nozzle 19 to provide additional propulsive thrust. The high, intermediate and low-pressure turbines respectively drive the high and intermediate pressure compressors 14, 13 and the fan 12 by suitable interconnecting shafts.

As will be appreciated by those of skill in the art of gas turbine engines, the engine's turbines 16, 17, 18 conventionally have a large number of individual turbine blades, those of the low pressure turbine being indicated at 24 in FIG. 1. The blades of each turbine have an advanced aerofoil shape are conventionally made from nickel-based superalloys. However, recent developments have led to experimentation with the use of intermetallic materials for turbine blades, and gamma titanium aluminide (TiAl) is considered particularly attractive for this purpose in the case of the low pressure turbine 18 which operates at a lower temperature than the high and intermediate pressure turbines 16, 17.

It has been proposed to cast the turbine blades 24 from gamma TiAl. However, as explained previously, the casting process can give rise to undesirable pores in the resulting component. Whilst hot isostatic pressing can be effective in removing pores which are deep within the component, or at least reducing their size to below an acceptable threshold, in the case of pores near the surface of the component the hot isostatic pressing can give rise to problematic undulations at the surface. It is therefore proposed to surface treat the cast component, which may be a turbine blade 24, according to the method of the present invention, embodiments of which will now be described in detail below. Whilst the invention is described below with specific reference to embodiments in which it is performed on a cast turbine blade 24, it is to be appreciated that the invention is not limited to implementation on turbine blades 24, and could be performed on other cast components.

Following initial casting of the turbine blade 24, the blade 24 is then cleaned and visually inspected to ensure complete removal of any surface contaminants. It is important to note that at this stage the turbine blade 24 is not subject to hot isostatic pressing.

Figure 2:
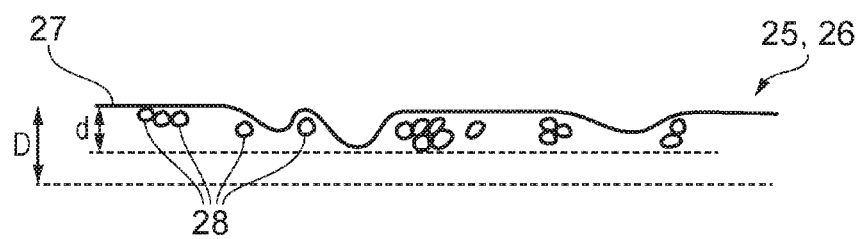
FIG. 2 is a schematic illustration depicting surface-connected and near-surface pores at the surface of a cast intermetallic component.

Once the turbine blade has been cleaned and inspected, one or more images are taken of the blade. This may involve capturing a stereo-optical image 25 of the blade 24, for use as a component-specific datum during subsequent steps in the method which involve the control of a laser beam. In currently preferred embodiments of the invention, an X-ray image 26 of the blade 24 is then captured which will show any porosity in the casting. It is proposed to superimpose the stereo-optical image 25 and the X-ray image 26, thereby effectively overlaying the X-ray image 26 on the stereo-optical image 25. FIG. 2 shows a schematic representation of part of the resulting superimposed images, formed from the stereo-optical image 25 and the X-ray image 26. In particular, it will be noted that FIG. 2 shows a region of the images in the vicinity of a surface 27 of the turbine blade 24.

As will be noted from FIG. 2, the X-ray image 26 shows up individual and clustered pores 28 near the surface 27 of the turbine blade 24. The image may thus be used as the basis of a step of analysing the blade 24 in order to identify potentially problematic pores 28 near the surface 27. More particularly, it is proposed to use the superimposed images 25, 26 in order to identify target pores 28 requiring rectification. The target pores may be near-surface pores 28 or surface-connected pores 28 which are open to the surface 27 of the blade 24.

The step of analysing the blade 24 may be carried out manually, via a simple visual assessment of the superimposed images 25, 26, or may alternatively be carried out automatically using a computer. In each case, the analysing step involves identifying the deepest potentially problematic pore or cluster of pores 28, and determining their depth d from the surface 27 of the blade 24. The maximum depth d of the target pores 28 is then compared to a predetermined threshold depth D measured from the surface 27 of the blade 24. If the maximum depth d of the target pores is greater than the threshold depth D, then the blade will need to be discarded because the pores 28 are too deep to be rectified by the method of the present invention without adversely affecting the lamellar structure of the intermetallic material and hence the mechanical properties of the turbine blade 24. However, if the maximum depth d of the target pores 28 is less than or equal to the threshold depth, then the surface 27 and its associated pores 28 may be rectified by the method of the present invention which, as will be described in more detail below, involves gentle local melting of the intermetallic material of the blade 24 down to the maximum depth d of the target pores 28 using one or more laser beams.

It has been determined that the threshold depth D should be no more than 300 µm, although in other embodiments it may be even lower; for example: 250 µm, 200 µm, or 150 µm.

Figure 3:
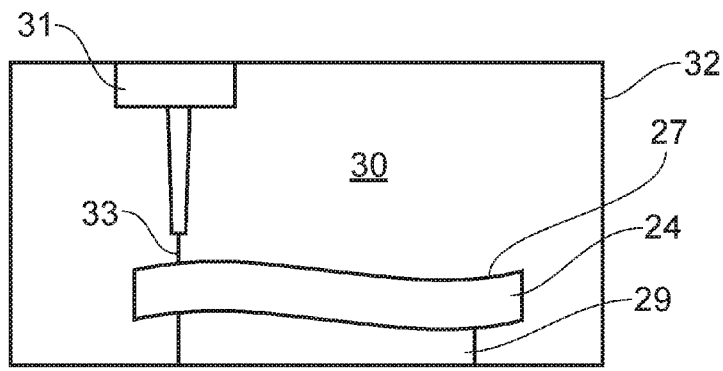
FIG. 3 is a schematic illustration showing a component being treated by a method in accordance with the present invention.

Following the above-described cleaning, inspecting, imaging and analysing steps, the turbine blade 24 is located onto a fixture arrangement 29 which is designed to hold the blade 24 securely as illustrated schematically in FIG. 3. It is to be appreciated, however, that in alternative embodiments the blade 24 could be located onto the fixture arrangement 29 prior to the imaging and/or analysing steps such that either or both of those steps could be performed with the blade 24 securely held by the fixture arrangement 29.

The fixture arrangement 29 and the blade 24 are then placed in an inert atmosphere 30 within which there is also provided a laser beam device 31 such as a laser diode. In preferred embodiments, the inert atmosphere 30 is provided inside a vacuum chamber 32 as illustrated schematically in FIG. 3. However, in other embodiments the inert atmosphere 30 could be provided inside a chamber charged with inert gas such as Argon. In this respect, it is to be noted that the inert atmosphere is one which has very little, and preferably no oxygen present. This is important to the preferred method because operation of the laser beam device 31 will be effective to heat the surface 27 of the blade 24 which, because it is made from intermetallic titanium, would otherwise absorb oxygen when it is heated.

The laser beam device 31 is operated within the inert atmosphere 30 to focus a laser beam 33 onto the surface 27 of the turbine blade 24. The laser beam device 31 and/or the fixture arrangement 29 is also manipulated and moved, for example under the control of a computer, so as to traverse the laser beam 33 over the surface 27. In this respect, it is to be noted that the laser beam 33 energizes the surface 27 of the turbine blade 24 so as to locally melt the intermetallic material of the blade 24 only in the region of its surface. The laser beam 33 is therefore controlled such that it energises the surface 27 of the turbine blade 24 in a somewhat gentle manner, and in particular so as to melt the intermetallic material only down to the maximum depth d of the target pores 28, as determined via the above-described analysing step. The depth to which the intermetallic material of the blade 24 is melted will thus be dependent on the analysis of the blade, and will thus be particular to the individual blade 24 being treated. As will also be appreciated, the depth to which the intermetallic material is melted will not exceed the threshold depth D, which may be, for example, 150 µm.

By gently melting the region of the intermetallic material local to the surface 27 of the turbine blade 24, where potentially problematic target pores 28 have been identified, the target pores in this region 28 will be transitioned to the surface of the blade and hence removed from the material or at least significantly reduced in diameter, whilst the underlying material deeper within the turbine blade 24 will be unaffected by the heat of the laser beam 33 and will hence retain its lamellar structure and useful mechanical properties such as fatigue strength. If the intermetallic material of the turbine blade 24 were to be heated more aggressively, and hence deeper into the blade 24, then the blade would lose such properties.

In more detail, operation of the laser beam device 31, and its resultant laser beam 33 may be effected by controlling various aspects of the beam 33 such as, for example: its power; its degree of focus; the shape of the beam; and the pulse period of the laser beam 33. It is envisaged that some or all of these characteristics of the beam 33 may be controlled automatically, for example by computer operated in accordance with features of the stereo-optical 25 and/or the x-ray image 26. For example, one or both of said images 25, 26 could be input into suitable CAD/CAM software on a computer and then used to control the laser beam 33.

As well as operating the laser beam 33 in a gentle manner with parameters resulting in low energy density so as not to melt the intermetallic material too deeply, it has also been found to be beneficial to permit only relatively slow cooling of the material after it has been heated via the laser beam 33. One way in which this can be achieved is by traversing the laser beam 33 across the surface 27 of the turbine blade 24 slowly, so that a region energised by the beam 33 is not allowed to cool too rapidly as would be the case if the beam was quickly moved away from the energised region.

Figure 4:
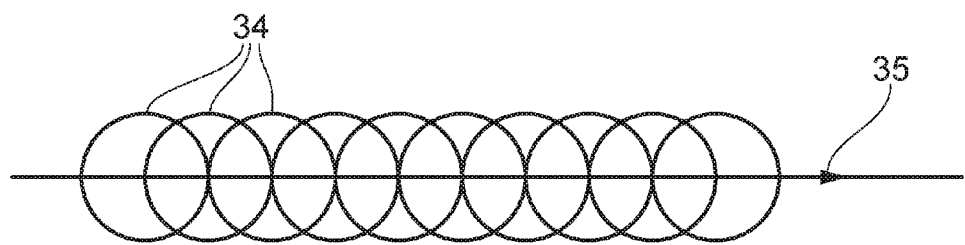
FIG. 4 is a schematic illustration showing a series of successive target areas which are energized in turn by a laser beam.

FIG. 4 illustrates schematically a series of discrete target areas 34 on the surface 27 of a turbine blade. The target areas 34 are energised successively by the laser beam 33 as the beam is traversed across the surface, as denoted by arrow 35. Each target area 34 is energised by the laser beam 33 for a discrete dwell period, before the laser beam is moved to the next successive target area 34. As will be noted, the target areas 34 each overlap their immediately preceding neighbour which means that a degree of heat energy is applied to the overlapped part of the preceding target area 34. This is effective in reducing the rate of cooling of each region of the blade's surface 27. It should be noted in this regard, that whilst FIG. 4 specifically denotes a generally circular beam shape which is effective to energise circular target areas 34 on the surface 27 of the turbine blade, other alternative beam shapes such as oval, rectangular etc. could be used instead.

After the above-described method of laser treatment has been completed, such that the target pores 28 near the surface 27 of the turbine blade have been removed or at least reduced in size, the component may then by subjected to hot isostatic pressing in the usual manner. Because the method of the present invention is effective to rectify the near-surface or surface-connected porosity, a subsequent hot isostatic pressing step will not result in the creation of an undulating surface as has been the case in the prior art.

Figure 5:
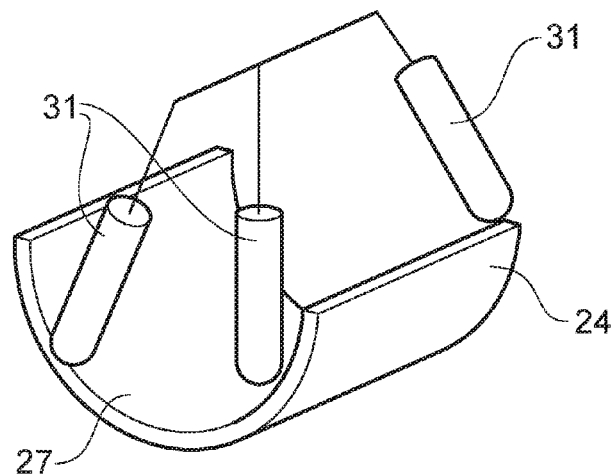
FIG. 5 is a schematic illustration showing a component being treated by a method involving the simultaneous use of a number of laser beams.

It is to be noted that the above-described method may be implemented by the use of a plurality of laser beam devices 32 and associated laser beams 33. For example, it is envisaged that a plurality of laser beams 33 could be operated and controlled simultaneously, either to energise respective regions of the same component 24, as illustrated schematically in FIG. 5, or to treat a plurality of respective components simultaneously.

It is also proposed that in some implementations of the present invention a surface of the turbine blade 24 or other component, opposite to the surface 27 being energised and heated by the laser beam 33, may have a balanced heat load applied to it during operation of the laser beam 33 in order to offset the heat load arising from the laser beam 33 and thereby avoid distortion of the component. Alternatively, or additionally, the turbine blade or other component 24 could be pre-tensioned during operation of the laser beam 33.

It is to be noted that whilst the present invention has been described above with specific reference to its use in surface-treating components formed from gamma TiAl, the invention is not limited to use only on components of this specific material. The method is also suitable for use on other types of intermetallic titanium, and also on other intermetallic materials more generally.

It is also to be appreciated that the method of the present invention can be employed during the manufacture of new cast intermetallic components, but also to salvage components which would otherwise need to be scrapped due to excessive surface-connected or near-surface porosity. Also, the method of the present invention could also be used after repair operations are performed on in-service cast intermetallic components, such as machining or polishing operations which remove surface material from a component and hence may expose existing pores in the component or bring such existing pores into the sensitive near-surface zone of the component.

It is to be noted that the method of the present invention uses a stereo-optical image and/or an X-ray image of the cast intermetallic component and does not use fluorescent penetrant inspection and/or etchants. Thus, the present invention additionally does not have to remove the chemicals used in fluorescent penetrant inspection and/or as an etchant and hence the risk of chemical contamination of the cast intermetallic component due to the difficulty of removing these chemicals from the surface pores in the component is obviated.

When used in this specification and claims, the terms "comprises" and "comprising" and variations thereof mean that the specified features, steps or integers are included. The terms are not to be interpreted to exclude the presence of other features, steps or integers.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A method of surface-treating a cast intermetallic titanium component, the method comprising the steps of:
    providing a cast intermetallic titanium component;
    placing the cast intermetallic titanium component in an inert atmosphere;
    focussing a laser beam on a surface of the cast intermetallic titanium component;
    traversing the laser beam over at least a region of said surface whilst the cast intermetallic titanium component is in said inert atmosphere; and
    controlling the laser beam during said traversing step so as to locally melt the intermetallic material of the cast component to a predetermined threshold depth of no more than 300 µm, as measured from said surface of the cast component,
    the method further including a step of analysing the cast component, prior to said steps of focussing and traversing the laser beam, in order to identify target surface-connected and/or near-surface pores in the cast component and determining the maximum depth of said target pores from the surface of the cast component; wherein said step of controlling the laser beam comprises operating the laser beam so as to locally melt the intermetallic material of the cast component to said maximum depth,
    the analysing step comprising comparing the maximum depth of the target pores to the predetermined threshold depth, if the maximum depth of the target pores is less than or equal to the predetermined threshold depth, then the laser beam is focussed on the surface of the cast component and the laser beam is traversed over at least the surface whilst the cast component is in said inert atmosphere.

2. A method according to claim 1, wherein the laser beam is controlled so as to locally melt the intermetallic material of the cast component to a depth of no more than 150 µm as measured from said surface of the cast component.

3. A method according to claim 1, wherein said step of analysing the cast component comprises capturing an image of the surface region of the cast component.

4. A method according to claim 3, wherein said image comprises a stereo-optical image.

5. A method according to claim 3, wherein said image comprises an X-ray image.

6. A method according to claim 3, wherein said step of controlling the laser beam comprises controlling the laser beam based on features of said image.

7. A method according to claim 3, wherein said step of analysing the cast component is performed manually.

8. A method according to claim 3, wherein said step of analysing the cast component is performed automatically using a computer.

9. A method according to claim 1, wherein said focussing step comprises focussing the laser beam such that it energizes a target area on the surface of the cast component, and wherein said step of traversing comprises moving the laser beam incrementally relative to the cast component so as to energize successive said target areas on the surface of the cast component; each target area being energized for a discrete dwell period and overlapping at least the immediately preceding target area.

10. A method according to claim 1, wherein said step of traversing comprises movement of the laser beam.

11. A method according to claim 1, wherein said step of traversing comprises movement of the cast component.

12. A method according to claim 1, wherein a heat load is applied to said cast component during said focussing, traversing and controlling steps, said heat load being applied to the opposite side of the cast component to that on which said surface is provided.

13. A method according to claim 1, wherein said cast component is pre-tensioned during said focussing, traversing and controlling steps.

14. A method according to claim 1, wherein said step of controlling the laser beam comprises controlling at least one of: the power; the focus; the beam-shape; and the pulse period of the laser beam.

15. A method according to claim 1, performed on a cast component which is formed of gamma titanium aluminide.

16. A method according to claim 1, performed on a cast component in the form of a turbine blade for a gas turbine engine.

17. A method according to claim 1, wherein said step of placing the cast component in an inert atmosphere comprises placing the cast component in a vacuum chamber.

18. A method according to claim 1, comprising the use of a plurality of said laser beams.

19. A method according to claim 1, performed simultaneously on a plurality of said cast components.

20. A method according to claim 1, further comprising hot isostatic pressing the cast component after the steps of focussing and traversing the laser beam.

21. A method of surface-treating a cast intermetallic titanium component, the method comprising the steps of:
    providing a cast intermetallic titanium component;
    placing the cast intermetallic titanium component in an inert atmosphere;
    focussing a laser beam on a surface of the cast intermetallic titanium component; traversing the laser beam over at least a region of said surface whilst the cast intermetallic titanium component is in said inert atmosphere; and
    controlling the laser beam during said traversing step so as to locally melt the intermetallic material of the cast component to a predetermined threshold depth of no more than 300 µm, as measured from said surface of the cast component, and hot isostatic pressing the cast component, the method further including a step of analysing the cast component, prior to said steps of focussing and traversing the laser beam, in order to identify target surface-connected and/or near-surface pores in the cast component and determining the maximum depth of said target pores from the surface of the cast component; wherein said step of controlling the laser beam comprises operating the laser beam so as to locally melt the intermetallic material of the cast component to said maximum depth, the step of analysing the component comprises capturing an image of the surface region of the component and the image is selected from the group consisting of a stereo-optical image, an X-ray image and a combination of a stereo-optical image and an X-ray image.

* * * * *